(12) United States Patent
Thomas et al.

(10) Patent No.: US 9,055,999 B2
(45) Date of Patent: Jun. 16, 2015

(54) RADIOPAQUE MARKERS FOR VISUALIZING AN EDGE OF AN ENDOVASCULAR GRAFT

(71) Applicant: Medtronic Vascular, inc., Santa Rosa, CA (US)

(72) Inventors: Richard Thomas, Santa Rosa, CA (US); Dustin Sneed, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 43 days.

(21) Appl. No.: 13/743,676

(22) Filed: Jan. 17, 2013

(65) Prior Publication Data

US 2014/0200656 A1   Jul. 17, 2014

(51) Int. Cl.
*A61F 2/06* (2013.01)
*A61F 2/07* (2013.01)

(52) U.S. Cl.
CPC ... *A61F 2/06* (2013.01); *A61F 2/07* (2013.01); *A61F 2002/065* (2013.01); *A61F 2250/0098* (2013.01)

(58) Field of Classification Search
CPC .............................................. A61F 2250/0098
USPC ........................................................ 623/1.34
See application file for complete search history.

(56) References Cited

U.S. PATENT DOCUMENTS

| | | | | |
|---|---|---|---|---|
| 5,370,691 A | * | 12/1994 | Samson | 623/1.22 |
| 5,649,978 A | * | 7/1997 | Samson | 606/198 |
| 5,741,327 A | * | 4/1998 | Frantzen | 623/1.34 |
| 5,824,042 A | | 10/1998 | Lombardi et al. | |
| 6,203,568 B1 | * | 3/2001 | Lombardi et al. | 623/1.13 |
| 8,292,950 B2 | * | 10/2012 | Dorn et al. | 623/1.35 |
| 8,545,548 B2 | * | 10/2013 | Lorenzo | 623/1.34 |
| 2002/0095205 A1 | | 7/2002 | Edwin et al. | |
| 2003/0060872 A1 | * | 3/2003 | Gomringer et al. | 623/1.15 |
| 2003/0176912 A1 | | 9/2003 | Chuter et al. | |
| 2004/0015229 A1 | * | 1/2004 | Fulkerson et al. | 623/1.22 |
| 2004/0073291 A1 | * | 4/2004 | Brown et al. | 623/1.15 |
| 2004/0254637 A1 | * | 12/2004 | Yang et al. | 623/1.34 |
| 2005/0004653 A1 | | 1/2005 | Gerberding | |
| 2008/0215134 A1 | | 9/2008 | Lawrence-Brown | |
| 2008/0243227 A1 | * | 10/2008 | Lorenzo | 623/1.15 |
| 2009/0264990 A1 | | 10/2009 | Bruszewski et al. | |
| 2010/0114298 A1 | * | 5/2010 | Dorn et al. | 623/1.23 |
| 2010/0249896 A1 | * | 9/2010 | Sugimoto et al. | 623/1.11 |
| 2012/0035714 A1 | | 2/2012 | Ducke et al. | |

FOREIGN PATENT DOCUMENTS

WO    WO01/72240    10/2001

OTHER PUBLICATIONS

International Search Report and Written Opinion, Int'l Appl. No. PCT/US2014/010886, dated Apr. 4, 2014.

* cited by examiner

*Primary Examiner* — Jacqueline Woznicki

(57) ABSTRACT

An endovascular prosthesis is disclosed that includes a tubular graft and a radiopaque marker attached to envelop or enfold an edge of the tubular graft. A first segment of the radiopaque marker extends against an interior surface of the tubular graft and a second segment of the radiopaque marker extends against an exterior surface of the tubular graft such that the first and second segments sandwich or straddle the edge of the tubular graft. The radiopaque marker may include a living hinge that demarcates the first and second segments and aligns with the tubular graft edge when the radiopaque marker is attached thereto. The radiopaque marker may have a substantially U shape with the first and second segments biased toward each other by an end segment such that the end segment aligns with the tubular graft edge when the radiopaque marker is attached thereto.

10 Claims, 5 Drawing Sheets

RADIOPAQUE MARKERS FOR VISUALIZING AN EDGE OF AN ENDOVASCULAR GRAFT

FIELD OF THE INVENTION

The present invention relates general to endovascular grafts, and more particularly to radiopaque markers for visualizing an edge of an endovascular graft under fluoroscopy.

BACKGROUND OF THE INVENTION

Tubular prostheses, such as stents, grafts, and stent-grafts are known for treating abnormalities in various passageways of the human body. In vascular applications, these devices often are used to replace or bypass occluded, diseased or damaged blood vessels such as stenotic or aneurysmal vessels. For example, it is well known to use stent-grafts of a biocompatible graft material supported by a framework, for e.g., one or more stent or stent-like structures, to treat or isolate aneurysms. The framework provides mechanical support and the graft material or liner provides a blood barrier. When implanting a stent-graft, the stent-graft typically is placed so that one end of the stent-graft is situated proximal to or upstream of the diseased portion of the vessel and the other end of the stent-graft is situated distal to or downstream of the diseased portion of the vessel. In this manner, the stent-graft extends through and spans the aneurysmal sac and extends beyond the proximal and distal ends thereof to replace or bypass the dilated wall.

Such tubular prostheses are known to be implanted in either an open surgical procedure or by a minimally invasive endovascular/endoluminal approach. Minimally invasive endovascular stent-grafts for use in treating aneurysms are often preferred over traditional open surgery techniques where the diseased vessel is surgically opened, and a graft is sutured into position bypassing the aneurysm. The endovascular approach generally involves opening a vein or artery with a needle, inserting a guidewire into the vein or artery through the lumen of the needle, withdrawing the needle, inserting over the guidewire a dilator located inside an associated sheath introducer having a hemostasis valve, removing the dilator and inserting a delivery catheter through the hemostasis valve and sheath introducer into the blood vessel. The delivery catheter with the stent-graft secured therein may then be routed through the vasculature to a treatment site. For example, a stent-graft delivery catheter loaded with a stent-graft can be percutaneously introduced into the vasculature, for e.g., into a femoral artery, and the stent-graft delivered endovascularly to a treatment site, such as across an aneurysm, where it is then deployed.

Some type of visualization of the stent-graft during deployment at the treatment site is necessary, particularly when treating an aneurysm as proper placement of a proximal anchor stent(s) against a seal or landing zone, i.e., a patent portion of the vessel wall proximal of the aneurysm, is critical while at the same time the clinician must avoid inadvertently covering one or more branch vessels that may be near the aneurysm with the graft material of the stent-graft. Generally, one or both ends of the stent-graft will have one or more radiopaque markers sewn thereon, either to the graft material and/or a stent structure, and the clinician will utilize a fluoroscope to observe the deployment by means of X-rays to attempt to assure optimal placement.

Radiopaque markers are typically sewn onto the graft material of a stent-graft and are not sewn or otherwise attached to the stent structure thereof, which is generally either mounted on or within the graft material, because doing so can add undesirable bulk and increase an overall delivery profile of the stent-graft. However radiopaque markers that are sewn onto the graft material of the stent-graft must typically be offset by a few millimeters from a leading or true edge of the graft material due to concerns related to the interaction of the sutures with the edge of the graft material, such as fraying of the edge of the graft material which could result in the radiopaque marker separating therefrom. As a result, the clinician must estimate under fluoroscopy the exact location of the graft material edge when deploying the stent-graft at the treatment site.

An accurate estimation of the leading or true edge of the graft material of the stent-graft may become especially critical in anatomies where short landing or seal zones are present, such as a landing or seal zone near the renal arteries. More particularly, for e.g., when treating an abdominal aortic aneurysm (AAA) that is distal of the renal arteries with a diameter of the renal arteries being typically on the order of 4 mm to 7 mm, the few millimeter offset between the radiopaque marker and the graft material edge may become significant as an inaccurate estimation of the distance therebetween could result in the stent-graft being inadvertently deployed with the leading edge of the graft material thereof partially or entirely covering one or both of the renal arteries. The same is true for placement of a stent-graft for treating a thoracic aortic aneurysm (TAA) that occurs distal of the left subclavian artery (LSA) and the left common carotid (LCC), where improper or inadvertent placement of an edge of the graft material of the stent-graft could interfere with blood flow into these important arteries.

Thus a need exists in the art to provide improved means for visualizing the leading or true edge of the graft material of an endovascular prosthesis, such as a stent-graft, thus allowing for more accurate device placement.

BRIEF SUMMARY OF THE INVENTION

Embodiments hereof are directed to an endovascular prosthesis that includes a tubular graft of a graft material having a proximal end, a distal end, an interior surface and an exterior surface. A radiopaque marker is attached to one of the proximal and distal ends of the tubular graft of the prosthesis such that the radiopaque marker envelops an edge of the graft material. A first segment of the radiopaque marker is positioned to extend against the interior surface of the tubular graft and a second segment of the radiopaque marker is positioned to extend against the exterior surface of the tubular graft. In an embodiment, a living hinge demarcates the first and second segments of the radiopaque marker and aligns with the edge of the graft material such that the first and second segments of the radiopaque marker straddle the graft material therebetween. In another embodiment, the radiopaque marker has a substantially U shape with the first and second segments biased toward each other by an end segment thereof, wherein the end segment aligns with and enfolds the edge of the graft material of the tubular graft with the first and second segments of the radiopaque marker sandwiching the graft material therebetween.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. Regarding "proximal" and "distal" positions referenced herein, a proximal end of an endovascular prosthesis, e.g., stent-graft, is the end closest to the heart by way of blood flow path whereas a distal end of the endovascular prosthesis is the end furthest away from the heart during deployment. In contrast, a distal end of the stent-graft delivery system or other associated delivery apparatus is usually identified as the end that is farthest from the operator, while a proximal end of the delivery system and devices is the end nearest the operator or handle of the catheter. In addition, the term "self-expanding" is used in the following description with reference to one or more stent structures of the endovascular prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of embodiments hereof are in the context of treatment of blood vessels such as the aorta, coronary, carotid and renal arteries, the invention may also be used in any other body passageways where it is deemed useful. Furthermore, there is no intention to be bound by any expressed or implied theory presented in the preceding technical field, background, brief summary or the following detailed description.

Figure 1:
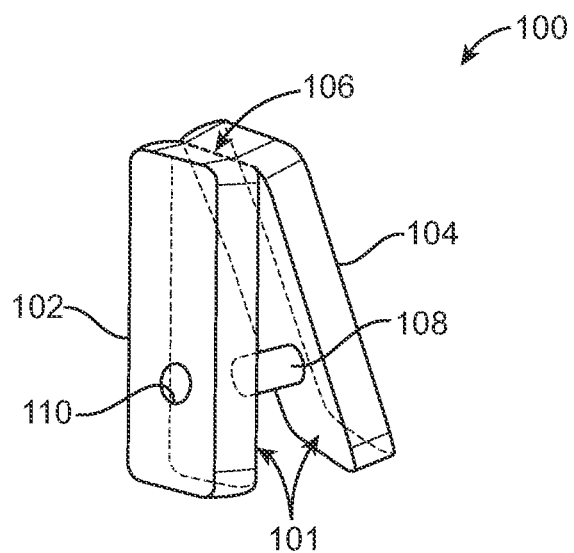
FIG. 1 is a perspective view of a radiopaque marker in accordance with an embodiment hereof.
Figure 2:
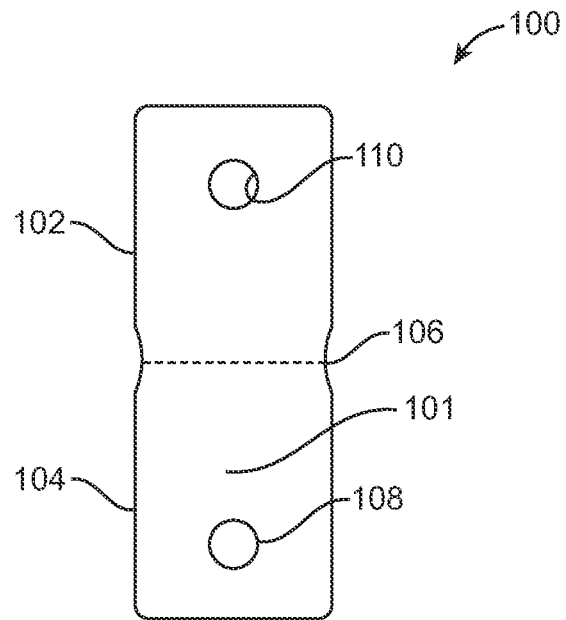
FIG. 2 depicts the radiopaque marker of FIG. 1 in a laid-open configuration.

FIG. 1 is a perspective view of a radiopaque marker 100 in accordance with an embodiment hereof, with FIG. 2 depicting radiopaque marker 100 in a laid-open configuration. Radiopaque marker 100 is configured to envelop or enfold an edge of a graft material of an endovascular prosthesis, such as a stent-graft so as to permit visualization of the leading or true edge of the prosthesis as will be described in more detail below. As used to describe embodiments hereof, by "envelop" or "enfold" the edge of the graft material it is meant that radiopaque marker 100 surrounds or wraps around the edge of the graft material to which it is attached such that radiopaque marker 100 may be considered to straddle the edge of the prosthesis with one section or segment of radiopaque marker 100 extending on a first side or surface of the graft material and another section or segment of radiopaque marker 100 extending on a second side or surface of the graft material. In an embodiment, radiopaque marker 100 has a first or interior segment 102 for extending against a first side or surface of the graft material and a second or exterior segment 104 for extending against a second side or surface of the graft material with a living hinge 106 being defined therebetween that aligns with or sits along the edge of the graft material. Living hinge 106 is a thin flexible hinge or flexure bearing made from the same material as the two more rigid first and second segments 102, 104 that it connects. In an embodiment, radiopaque marker 100 is formed or cut from a radiopaque material into a suitable shape, such as the substantially rectangular shape shown in FIG. 2, and a depth of a midsection thereof is thinned or a width of the midsection is waisted, narrowed or notched to create living hinge 106. Living hinge 106 functions to permit first and second segments 102, 104 to bend or swing toward each other along the line of the hinge for attachment to a graft component of a stent-graft.

First and second segments 102, 104 and living hinge 106 of radiopaque marker 100 define a graft contact surface 101 for contacting a corresponding surface of the graft material when radiopaque marker 100 is attached to an edge of the stent-graft. In the embodiment of FIGS. 1 and 2, second segment 104 of radiopaque marker 100 includes a post or pin 108 extending from contact surface 101 and first segment 102 of radiopaque marker 100 includes a corresponding aperture 110 therethrough within which post 108 is inserted so as to clamp or otherwise attach radiopaque marker 100 to the graft material of a tubular graft component.

Figure 3:
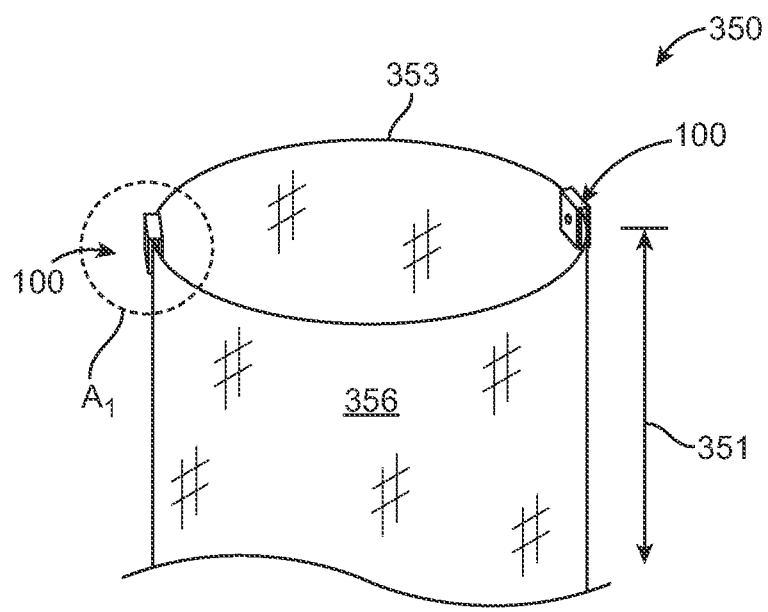
FIG. 3 depicts the radiopaque marker of FIG. 1 attached along a leading edge of a stent-graft.

A proximal end portion 351 of a stent-graft 350 is depicted in FIG. 3 with radiopaque markers 100 attached to a leading or proximal edge 353 of a tubular graft component 356 of stent-graft 350. As would be understood by one of skill in the art, stent-graft 350 includes one or more self-expanding stents or sinusoidal rings (not shown) for supporting a blood flow lumen defined by tubular graft component 356 and for anchoring and sealing stent-graft 350 at a landing zone. In embodiments hereof, tubular graft component 356 may be formed from any suitable biocompatible graft material, for example and not limited to, a low-porosity woven or knit polyester, DACRON material, expanded polytetrafluoroethylene (ePTFE), polyurethane, silicone, ultra high molecular weight polyethylene, or other suitable materials.

Figure 3A:
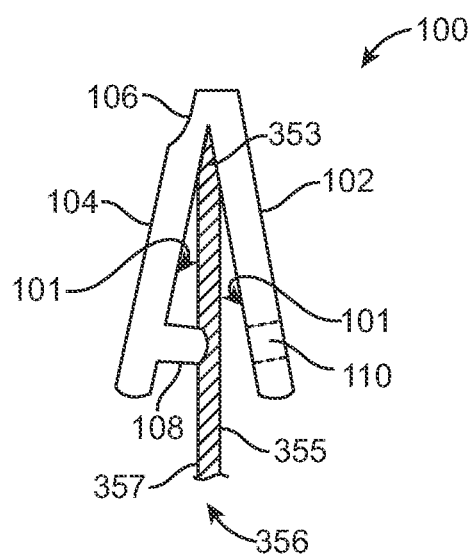
FIG. 3A is an enlarged sectional view of a portion of a leading edge of the stent-graft shown in FIG. 3 with the radiopaque marker of FIG. 1 positioned to be attached thereto.

With reference to FIG. 3A, which is an enlarged view of area A₁ of FIG. 3, each radiopaque marker 100 is attached to enfold or envelop a leading edge 353 of the graft material that forms tubular graft component 356. More particularly, graft contact surface 101 of radiopaque marker first segment 102 is positioned to extend against an interior surface 355 of tubular graft component 356 and contact surface 101 of radiopaque marker second segment 104 is positioned to extend against an exterior surface 357 of tubular graft component 356 such that living hinge 106 aligns with or extends along leading edge 353 of tubular graft component 356. Post 108 pierces the graft material of tubular graft component 356 and is received within aperture 110 to secure radiopaque marker 100 thereto. In an embodiment, post 108 functions as a rivet to lock first and second segments 102, 104 together with the end of post 108 that extends from aperture 110 being bucked or otherwise deformed to have an expanded diameter, relative to the original diameter of post 108, to hold post 108 in place within aperture 110 and to thereby prevent radiopaque marker 100 from being dislodged from the graft material.

In another embodiment (not shown), post 108 may be a separate component that slides within corresponding apertures 110 in first and second segments 102, 104 with each end of the post 108 being bucked or otherwise deformed to have an expanded diameter, relative to the original diameter of post 108, to hold post 108 in place within the corresponding apertures 110 with the graft material of tubular graft component 356 secured between first and second segments 102, 104. In another embodiment (not shown), post 108 may be a separate two-piece fitting that has a male component and a female component, wherein the female component slides within the corresponding apertures 110 of first and second segments 102, 104 and the male component compresses within the female component to join the first and second segments 102, 104 together with the graft material of tubular graft component 356 secured between first and second segments 102, 104.

In the embodiment of FIG. 3, two radiopaque markers 100 are depicted at two opposing points along a perimeter of stent-graft 350 for marking, and therefore visualizing, leading edge 353 during positioning and deployment of stent-graft 350 at a treatment site. In other embodiments, any suitable number of radiopaque markers 100 may be employed along a leading edge of stent-graft 350. Further although radiopaque marker 100 is described as being along a leading edge 353 on a proximal end portion 351 of stent-graft 100 this is by way of example and not limitation, and as such radiopaque markers 100 may also be disposed along a trailing or distal end of stent-graft 100 as may be desirable in certain interventional applications without departing from the scope hereof. Further it would be understood by one of skill in the art after consideration of the disclosure hereof, that first and second segments 102, 104 of radiopaque marker 100 may be reversed when being attached to edge 353 of stent-graft 350, i.e., first segment 102 being positioned to extend along an exterior surface 357 of tubular graft component 356 and second segment 104 being positioned to extend along an interior surface 355 of tubular graft component 356 without departing from the scope hereof.

Figure 4:
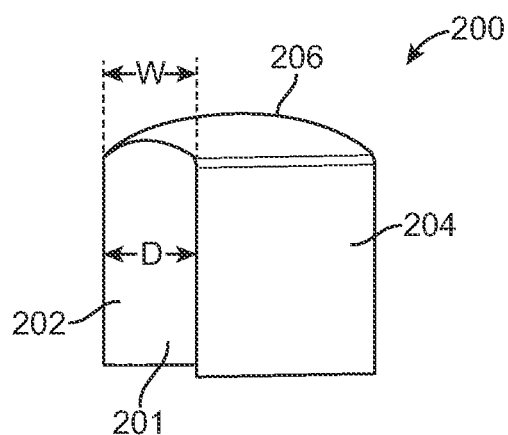
FIG. 4 is a perspective view of a radiopaque marker in accordance with another embodiment hereof.
Figure 5:
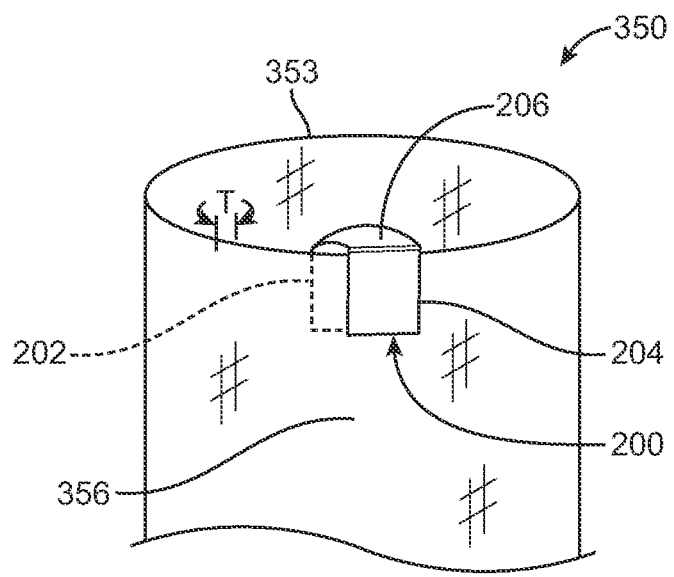
FIG. 5 depicts the radiopaque marker of FIG. 4 attached along a leading edge of a stent-graft.

FIG. 4 is a perspective view of a radiopaque marker 200 in accordance with another embodiment hereof, with FIG. 5 depicting radiopaque marker 200 attached along leading edge 353 of stent-graft 350. Radiopaque marker 200 may be considered to have a generally U or C shape with an end segment 206 demarcating first and second opposing segments 202, 204. Inwardly facing surfaces of first and second segments 202, 204 and end segment 206 of radiopaque marker 200 define a graft contact surface 201 for contacting the corresponding surfaces of the graft material when radiopaque marker 200 is attached to an edge of a stent-graft. With reference to FIG. 5, radiopaque marker 200 is attached to enfold or envelop leading edge 353 of the graft material that forms tubular graft component 356. More particularly, graft contact surface 201 of first and second segments 202, 204 of radiopaque marker 200 are positioned to extend against an interior and exterior surface of tubular graft component 356, respectively, such that end segment 206 aligns with and enfolds leading edge 353 of tubular graft component 356. In an embodiment, radiopaque marker 200 functions as a clip with end segment 206 being formed to bias first and second segments 202, 204 toward each other to sandwich the graft material of graft component 356 therebetween. In another embodiment, a width W of end segment 206 and thus a distance D between graft contact surfaces 201 of first and second segments 202, 204 are sized such that radiopaque marker 200 has an interference or friction fit with the graft material of graft component 356. In an embodiment, width W and distance D are less than a thickness T of the graft material with a thickness T of the graft material being selected from a range of 0.002 mm to 0.010 mm to provide an interference or friction fit therebetween. In another embodiment, radiopaque marker 200 is slid onto leading edge 353 of tubular graft component 356 of stent-graft 350 at a suitable location until end segment 206 aligns with and enfolds leading edge 353 and then first and second segments 202, 204 of radiopaque marker 200 are crimped together or otherwise plastically deformed with the graft material of graft component 356 sandwiched therebetween.

Figure 6:
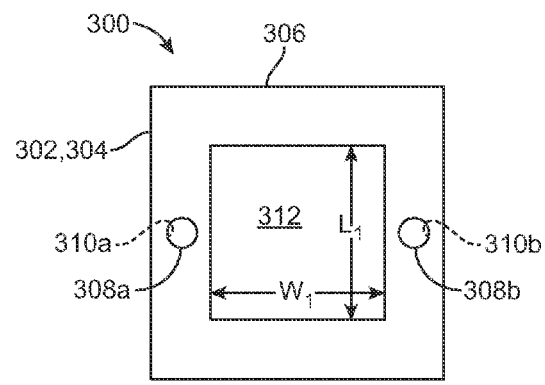
FIGS. 6 and 7 are side views of complementing shaped radiopaque markers in accordance with another embodiment hereof.
Figure 7:
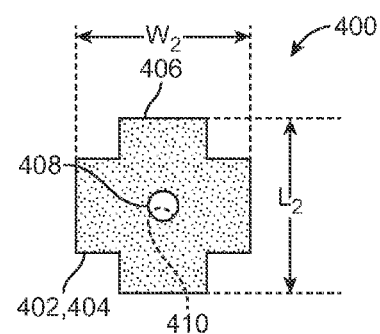

FIGS. 6 and 7 are side views of radiopaque markers 300, 400 in accordance with another embodiment hereof. Similar to the embodiment of FIG. 1, radiopaque markers 300, 400 have first and second segments with a living hinge therebetween and a post and aperture attachment mechanism. With reference to radiopaque marker 300 depicted in FIG. 6, first and second sides or segments 302, 304 have a living hinge 306 forming a common edge therebetween. In addition, each of first and second segments 302, 304 includes a side opening 312 therethrough that has a square shape or profile. One of first and second segments 302, 304 includes posts 308a, 308b extending from a graft contacting surface thereof and the other of first and second segments 302, 304 includes corresponding apertures 310a, 310b for receiving posts 308a, 308b therein when radiopaque marker 300 is attached to an edge of a graft component. With reference to radiopaque marker 400 depicted in FIG. 7, each of first and second segments 402, 404 of radiopaque marker 400 has a cross or X shape or perimetrical profile with living hinge 406 forming a common edge therebetween. One of first and second segments 402, 404 includes post 408 extending from a graft contacting surface thereof and the other of first and second segments 402, 404 includes corresponding aperture 410 for receiving post 408 therein when radiopaque marker 400 is attached to an edge of a graft component. In each of the embodiments depicted in FIGS. 6 and 7, posts 308a, 308b, 408 may function as a rivet to hold the respective radiopaque marker 300, 400 to an edge of the graft material of a graft component as described above with reference to post 108 of radiopaque marker 100.

Each of radiopaque markers 300, 400 may be attached to enfold or envelop a leading edge 353 of the graft material that forms tubular graft component 356. More particularly, the graft contact surfaces of first segments 302, 402 may be positioned to extend against an interior surface of tubular graft component 356 and the graft contact surfaces of second segments 304, 404 may be positioned to extend against an exterior surface of tubular graft component 356 such that a respective living hinge 306, 406 aligns with or extends along leading edge 353 of tubular graft component 356. As in the embodiment of FIG. 1, each of posts 308a, 308b, 408 pierce the graft material of tubular graft component 356 and is received within a respective aperture 310a, 310b, 410 to secure the respective radiopaque marker 300, 400 thereto.

Radiopaque markers 300, 400 may be used individually to aid in visualizing the true edge of a stent-graft as similarly described with reference to the previous embodiments or may be used in a coordinated fashion on a leading edge of the stent-graft to not only aid in visualizing the true edge of the stent graft but also to enable a clinician to adjust for parallax. A C-arm is a mobile fluoroscopic imaging system that is used in minimally invasive procedures to visualize a prosthesis and the interventional devices needed to deploy the prosthesis as would be understood by one of skill in the art. The phenomena of parallax can result in a prosthesis being improperly deployed and may be due to a position of the C-arm and a fluoroscopic ray therefrom that does not produce a true anteroposterior image but instead produces an image at an angle thereto.

Figure 8:
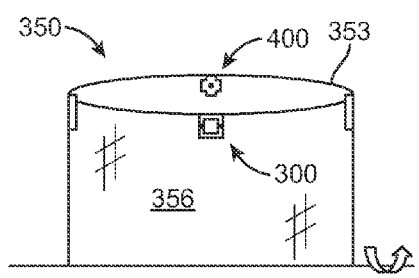
FIGS. 8 and 9 depict the radiopaque markers of FIGS. 6 and 7 attached on opposite sides of a stent-graft along a leading edge thereof so as to permit a clinician to visualize a leading edge of the stent-graft and to adjust for parallax.
Figure 9:
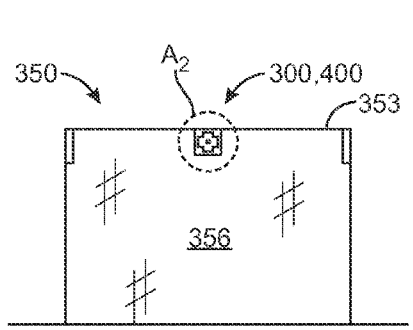

FIGS. 8 and 9 depict radiopaque markers 300, 400 attached on opposite sides of stent-graft 350 along leading edge 353 of graft component 356 thereof, or in other words at diametrically opposed positions along leading edge 353 that are separated by 180°. The diametrical opposition of radiopaque markers 300, 400 permits a clinician to visualize the leading edge of the stent-graft and to adjust for parallax. In the embodiment depicted in FIGS. 8, 9 and 9A, square opening 312 of radiopaque marker 300 has a length $L_1$ and a width $W_1$ that are substantially equal to a length $L_2$ and a width $W_2$ of cross-shaped radiopaque marker 400, such that radiopaque markers 300, 400 may be considered to have complementing shapes or profiles.

Figure 9A:
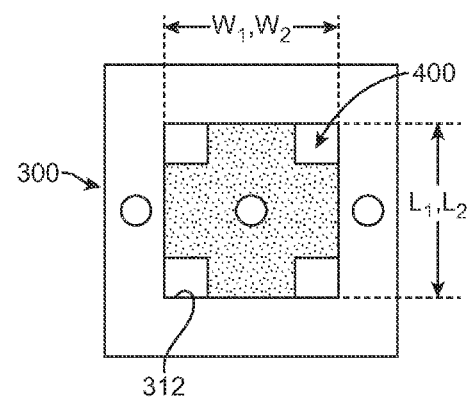
FIG. 9A is an enlarged view of the aligned radiopaque markers depicted in FIG. 9.

Under fluoroscopy, if radiopaque markers 300, 400 on opposing sides of stent-graft 350 appear to be displaced relative to each other so as to be separately visualized by a clinician, such as shown in FIG. 8, the clinician will know that the stent-graft is not being viewed correctly due to parallax and that an adjustment of the C-arm is in order. However upon visualizing under fluoroscopy the cross-shaped radiopaque marker 400 completely encapsulated within square opening 312 of radiopaque marker 300, such as shown in FIG. 9, than the clinician is assured that stent-graft 350 is being viewed without parallax, i.e., "directly on" so as to be normal to an edge of the stent graft or at a substantially 90° angle to a longitudinal axis thereof. FIG. 9A is an enlarged view of an area $A_2$ of stent-graft 350 in FIG. 9 depicting radiopaque marker 400 aligned or encapsulated within opening 312 of radiopaque marker 300 to illustrate a fluoroscopic view that indicates no parallax in the image.

In embodiments hereof, radiopaque markers 100, 200, 300, 400 may be formed as a unitary structure by first machining or stamping a thin sheet of radiopaque material, for instance, into a desired laid-open shape that defines mirror first and second segments. Thereafter another forming step may be performed to bend or otherwise fold the laid-open shape into a final form for radiopaque markers 100, 200, 300, 400 that will envelop or enfold an edge of the stent-graft. Additional processing steps may also be taken to provide a living hinge in accordance with embodiments hereof, if desired. Posts 108, 308, 408 may be attached to or formed as an integral structure with radiopaque markers 100, 200, 300, 400 by MIM or machining. In another embodiment, radiopaque markers 100, 200, 300, 400 may be formed with corresponding apertures in opposing segments thereof with an extruder rod dimensioned to have an interference fit with the apertures being utilized to secure the radiopaque marker to an edge of the graft material of the stent-graft. In embodiments hereof, radiopaque markers 100, 200, 300, 400 may be formed from a radiopaque material, such as tantalum, platinum-iridium, gold, iridium, palladium, rhodium, titanium, tungsten and alloys thereof.

Figures 10, 11:
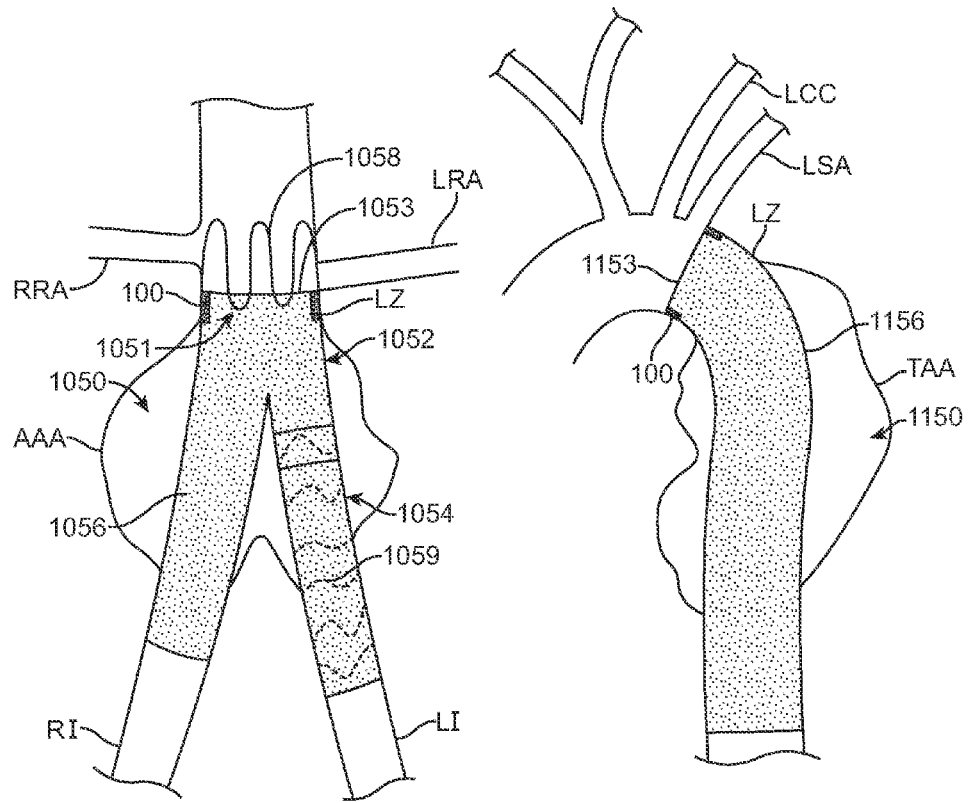
FIGS. 10 and 11 depict the radiopaque marker of FIG. 1 on various stent-grafts for use in treating aortic aneurysms proximate to branch vessels.

FIGS. 10 and 11 depict radiopaque marker 100 attached to an edge of a graft material of various stent-grafts for use in treating aortic aneurysms that are proximate to branch vessels. More particularly FIG. 10 depicts a modular bifurcated stent-graft 1050 for treating an abdominal aortic aneurysm (AAA) with a landing zone LZ that is distal of the renal arteries LRA, RRA and FIG. 11 depicts a tubular stent-graft 1150 for treating a thoracic aortic aneurysm (TAA) with a landing zone LZ that is distal of the left subclavian artery (LSA) and the left common carotid (LCC).

With reference to FIG. 10, modular bifurcated stent-graft 1050 includes a bifurcated main stent-graft 1052 and a limb stent-graft 1054. Main stent-graft 1052 constitutes a main blood flow lumen defined by a main trunk section that splits into two divergent blood flow lumens defined by respective leg sections thereof, with limb stent-graft 1054 defining a blood flow lumen that fluidly communicates with one of the divergent blood flow lumens. The main trunk section of bifurcated stent-graft 1052 is deployed within the aorta with a longer of the two leg sections positioned to extend within the right iliac artery (RI), and thereafter limb stent-graft 1054 is deployed to anchor within a shorter of the two leg sections to extend therefrom and into the left iliac artery (LI). Bifurcated main stent-graft 1052 is formed from a trouser-like or bifurcated graft component 1056 with a self-expanding anchoring stent or sinusoidal ring 1058 attached thereto. Radiopaque markers 100 are attached to enfold or envelop a leading edge 1053 of the graft material that forms bifurcated graft component 1056, as similarly described above. Anchoring stent 1058 proximally extends from a proximal end 1051 of main stent-graft 1052 for anchoring and sealing the stent-graft at the landing zone LZ proximal of the juxta-renal aneurysm. The single self-expanding anchoring stent 1058 shown in the embodiment of FIG. 10 is by way of example and not limitation, as a plurality of self-expanding stents or sinusoidal rings may be used along a length of the main trunk section and/or the leg sections of main stent-graft 1052 to serve various functions, such as anchoring, sealing and coupling, as would be apparent to one of skill in the art upon considering the complete disclosure hereof.

In embodiments hereof, bifurcated graft component 1056 may be formed from any suitable biocompatible graft material, for example and not limited to, a low-porosity woven or knit polyester, DACRON material, expanded polytetrafluoroethylene (ePTFE), polyurethane, silicone, ultra high molecular weight polyethylene, or other suitable materials. In embodiments hereof, an ENDURANT® type of bifurcated stent-graft available from Medtronic, Inc. that is delivered and deployed by a delivery system similar to the ENDURANT® stent-graft delivery system also available from Medtronic, Inc. may be adapted for use as main stent-graft 1052.

Limb stent-graft 1054 is a tube of graft material, such as any of the graft materials noted above, having self-expanding stents or sinusoidal rings 1059 for supporting a blood flow lumen defined by the graft material and for anchoring the limb stent-graft within the corresponding leg section of main stent-graft 1052. In embodiments hereof, an ENDURANT® type of stent-graft available from Medtronic, Inc. that is delivered and deployed by a delivery system similar to the ENDURANT® stent-graft delivery system also available from Medtronic, Inc. may be adapted for use as limb stent-graft 1054.

A method of deploying modular bifurcated stent-graft 1050 includes introducing a main delivery catheter via femoral access and advancing or tracking the main delivery catheter through the vasculature in a retrograde approach via the right iliac artery RI to a treatment site of the abdominal aortic aneurysm AAA. Bifurcated main stent-graft 1052 is initially maintained within the main delivery catheter in a radially compressed, delivery configuration. Under fluoroscopy, a clinician is able to visualize leading edge 1053 of main stent-graft 1052 to assure that the compressed main stent-graft 1052 is properly positioned at the treatment site with anchoring stent 1058 being located to expand into contact with the landing zone LZ and with leading edge 1053 of bifurcated graft component 1056 of main stent-graft 1052 being located distal of the ostium or openings of the left and right renal arteries LRA, RRA such that the graft material of bifurcated graft component 1056 will not interfere with blood flow into the branch vessels after deployment. It would be understood by one of skill in the art that proper placement of main stent-graft 1052 at the treatment site would also include assuring that a distal end of the longer leg section of the bifurcated graft component 1056 will extend within the right iliac artery RI prior to full deployment of bifurcated main stent-graft 1052. Thereafter, a branch or iliac delivery system is introduced and tracked through the vasculature with limb stent-graft 1054 mounted or compressed therein. The branch delivery system is positioned so as to deploy limb stent-graft 1054 to extend between the shorter leg section of the bifurcated graft component 1056 and the left iliac artery LI, as shown in FIG. 10, so as to implant modular bifurcated stent-graft 1050 for treating the abdominal aortic aneurysm AAA.

With reference to FIG. 11, tubular stent-graft 1150 includes a tubular graft component 1156 of a graft material, such as any of the graft materials noted above, having one or more self-expanding stent support structures (not shown) for supporting a blood flow lumen defined by tubular graft component 1156 and for anchoring the stent-graft at the landing zone LZ proximal of the thoracic aortic aneurysm (TAA). Radiopaque markers 100 are attached to enfold or envelop a leading edge 1153 of the graft material that forms tubular graft component 1156, as similarly described above. In embodiments hereof, an ENDURANT® type of stent-graft available from Medtronic, Inc. that is delivered and deployed by a delivery system similar to the ENDURANT® stent-graft delivery system also available from Medtronic, Inc. may be adapted for use as stent-graft 1150.

A method of deploying tubular stent-graft 1150 includes percutaneously introducing a stent-graft delivery system into the vasculature and advancing or tracking the stent-graft delivery system through the vasculature in either a retrograde or antegrade approach to a treatment site of the thoracic aortic aneurysm TAA. Stent-graft 1150 is initially maintained within the stent-graft delivery system in a radially compressed, delivery configuration. Under fluoroscopy, a clinician is able to visualize leading edge 1153 of stent-graft 1150 to assure that the compressed stent-graft is properly positioned at the treatment site to expand into contact with the landing zone LZ with leading edge 1153 of tubular graft component 1156 being situated distal of the ostium or openings of the left subclavian artery (LSA) and the left common carotid (LCC) such that the graft material of tubular graft component 1156 will not interfere with blood flow into the branch vessels after implantation of stent-graft 1150, as shown in FIG. 11.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An endovascular prosthesis comprising:
   a tubular graft of a graft material having a proximal end, a distal end, an interior surface and an exterior surface; and
   a radiopaque marker having a first segment and a second segment with a living hinge therebetween, wherein the living hinge is a thinned portion between the first and second segments, the radiopaque marker being attached to one of the proximal and distal ends of the tubular graft such that the radiopaque marker straddles a portion of a true edge of the graft material such that the living hinge lays along the true edge of the graft material with the first segment of the radiopaque marker being positioned to extend from the living hinge against the interior surface of the tubular graft and the second segment of the radiopaque marker being positioned to extend from the living hinge against the exterior surface of the tubular graft, wherein the living hinge permits the first and second segments to swing relative to each other when the radiopaque marker is unattached from the tubular graft.

2. The prosthesis of claim 1, wherein the tubular graft is a bifurcated graft component and the radiopaque marker straddles the true edge of the bifurcated graft component at the proximal end thereof.

3. The prosthesis of claim 1, wherein the first and second segments of the radiopaque marker include corresponding apertures through which a post is inserted so as to attach the radiopaque marker to the graft material.

4. The prosthesis of claim 1, wherein when unattached from the graft material the radiopaque marker has a laid-open configuration in which the first and second segments of the radiopaque marker extend in opposite directions from the living hinge.

5. The prosthesis of claim 4, wherein one of the first and second segments of the radiopaque marker includes a post extending from a contact surface thereof and the other of the first and second segments of the radiopaque marker includes a corresponding aperture therethrough within which the post is inserted so as to attach the radiopaque marker to the graft material.

6. The prosthesis of claim 1, wherein the radiopaque marker is attached to the proximal end of the stent-graft such that the true edge of the graft material is a leading edge of the tubular graft.

7. An endovascular prosthesis comprising:
   a tubular graft of a graft material having a proximal end, a distal end, an interior surface and an exterior surface; and
   a radiopaque marker attached to one of the proximal and distal ends of the tubular graft such that the radiopaque marker straddles a portion of a true edge of the graft material with a first segment of the radiopaque marker being positioned to extend against the interior surface of the tubular graft and a second segment of the radiopaque marker being positioned to extend against the exterior surface of the tubular graft, wherein one of the first and second segments of the radiopaque marker includes a post extending from a contact surface thereof and the other of the first and second segments of the radiopaque marker includes a corresponding aperture for receiving the post therein, such that the post pierces the graft material and is inserted within the aperture to attach the radiopaque marker to the graft material, wherein the first and second segments have a living hinge therebetween, wherein the living hinge is a thinned portion between the first and second segments.

8. The prosthesis of claim 7, wherein the living hinge lies along the true edge of the graft material such that the first and second segments of the radiopaque marker extend therefrom to straddle the graft material therebetween.

9. The prosthesis of claim 8, wherein when unattached from the graft material the radiopaque marker has a laid-open configuration in which the first and second segments of the radiopaque marker extend in opposite directions from the living hinge.

10. The prosthesis of claim 7, wherein the radiopaque marker is attached to the proximal end of the stent-graft such that the true edge of the graft material is a leading edge of the tubular graft.

* * * * *